United States Patent
Pellico

(12) 
(10) Patent No.: US 6,214,339 B1
(45) Date of Patent: Apr. 10, 2001

(54) DI-ENZYMATIC TREATMENT OF OUTER EAR INFECTION IN DOGS AND CATS

(76) Inventor: Michael A. Pellico, 2030 E. University Dr., Rancho Dominguez, CA (US) 90220

( * ) Notice: Subject to any disclaimer, the term of this patent is extended or adjusted under 35 U.S.C. 154(b) by 0 days.

(21) Appl. No.: 09/481,861

(22) Filed: Jan. 12, 2000

(51) Int. Cl.$^7$ .......................... A61K 38/44; A61K 38/47; C12N 9/02; C12N 9/14
(52) U.S. Cl. ...................... 424/94.4; 424/94.61; 435/189; 435/195
(58) Field of Search ................ 424/94.4, 94.61; 435/189, 195

(56) References Cited

U.S. PATENT DOCUMENTS

| | | | |
|---|---|---|---|
| 4,150,113 | 4/1979 | Hoogendorn | 424/50 |
| 4,178,362 | 12/1979 | Hoogendorn | 424/48 |
| 4,269,822 | 5/1981 | Pellico | 424/50 |
| 4,331,686 | 5/1982 | Djurickovic | 424/325 |
| 4,370,199 | 1/1983 | Orndorff | 162/161 |
| 4,537,764 | 8/1985 | Pellico | 424/50 |
| 4,564,519 | 1/1986 | Pellico | 424/48 |
| 4,576,817 | 3/1986 | Montgomery | 424/94 |
| 4,578,265 | 3/1986 | Pellico | 424/50 |
| 4,617,190 | 10/1986 | Montgomery | 426/61 |
| 5,066,497 | * 11/1991 | Witkin | 424/616 |
| 5,336,494 | 8/1994 | Pellico | 424/94.4 |
| 5,453,284 | 9/1995 | Pellico | 424/94.4 |
| 6,015,681 | 1/2000 | Ralls et al. | 435/7.32 |

\* cited by examiner

*Primary Examiner*—David M. Naff
*Assistant Examiner*—Mike Meller
(74) *Attorney, Agent, or Firm*—Donald Diamond

(57) ABSTRACT

Otitis externa is treated in dogs and cats by administering to the outer ear of the infected animal a dosage, effective to alleviate the symptoms of the infection, of a substantially non-aqueous, di-enzymatic therapeutic composition, in a liquid or gel fluid carrier. The composition contains an oxidizable substrate and an oxidoreductase enzyme specific to such substrate for producing hydrogen peroxide upon encountering the environment of the outer ear and further contains an iodide salt and and a peroxidatic peroxidase for interacting with the hydrogen peroxide to produce a hypoiodite biocidal agent. Any unbound water present in the composition is limited to an amount not more than about 1.0 wt. % to stabilize the composition against the production of hydrogen peroxide prior to aural application of the composition to enhance efficacy of treatment. An illustrative di-enzymatic composition composition contains glucose, glucose oxidase, potassium iodide and lactoperoxidase in a fluid mixture of glycerol and propylene glycol.

15 Claims, No Drawings

DI-ENZYMATIC TREATMENT OF OUTER EAR INFECTION IN DOGS AND CATS

BACKGROUND OF THE INVENTION

1. Field of the Invention

This invention relates to a method for treating outer ear infection in dogs and cats, otitis externa, with a di-enzymatic biocidal system in a substantially non-aqueous carrier. The di-enzymatic system, upon application to the outer ear, generates a hypoiodite which is a biocidal agent.

Otitis externa is a classification for infection of the external ear canal that begins at the outside opening of the ear and extends inward to the eardrum. Associated causes of otitis externa include bacteria, fungus, virus, yeast, and ear mites. The ears of dogs, particularly those with pendulous ears, and cats provide an environment for the infectious growth of bacteria, fungus and yeast because they are moist and warm and contain wax and other debris.

2. Related Art

It is disclosed in U.S. Pat. No. 4,331,686 (Djurickovic, 1982) that the most frequent microorganisms found in dogs affected with otitis externa are blastomyces, staphlococci, pytrosporum canis, pseudomonas, proteus and prototheca wickerhammii. This reference also discloses that the treatment of otitis externa has been based on prolonged deep instillation of antibiotics, antifungals, corticosteroids, and proteolytic enzymes.

The use of enzymatic systems to produce an antibacterial or biocidal effect is disclosed in the prior art.

U.S. Pat. No. 4,370,199 (Orndorff, 1983) discloses a method of killing and inhibiting the growth of microorganisms in industrial process streams by the addition of an enzymatically catalyzed biocide system which utilizes a plant dehydrogenase enzyme such as horseradish peroxidase in the presence of an oxidant such as hydrogen peroxide to oxidize a halide salt such as potassium iodide or sodium chloride to produce an oxidation product that is toxic to microorganisms.

U.S. Pat. No. 4,150,113 (Hoogendoorn et al., 1979) and U.S. Pat. No. 4,178,362 (Hoogendorn et al., 1979) disclose, respectively, an enzymatic toothpaste and an enzymatic chewable dentifrice containing glucose oxidase which acts on glucose present in saliva and tooth plaque to produce hydrogen peroxide. The patentees note that oral bacteria, through enzyme systems having SH-Groups, effect glycolysis of food products containing sugars and point out that lactoperoxidase, which is present in saliva, provides the means for transferring oxygen from hydrogen peroxide to oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

U.S. Pat No. 4,537,764 (Pellico et al., 1985) discloses an enzymatic dentifrice containing Beta-D-glucose and glucose oxidase for producing hydrogen peroxide upon oral application of the dentifrice, with pre-application stability being maintained by limiting any water in the dentifrice to not more than about 10 wt. % based on the weight of the dentifrice.

U.S. Pat. No. 4,576,817 (Montgomery et al., 1986) discloses enzymatic bandages and pads, for body contact applications, containing, for example, glucose oxidase which catalyzes the interaction of Beta-D-glucose, water and oxygen in the serum to produce hydrogen peroxide, and wherein the bandages and pads may further contain a peroxidase and an oxidizable salt such as thiocyanate, chloride or iodide salt of sodium or potassium which, in the presence of hydrogen peroxide and peroxidase are oxidized to thiocyanate (sic), hypochlorite and hypoiodite, respectively, that function as bacterial inhibitors.

U.S. Pat. No. 4,564,519 (Pellico et al., 1986) discloses a di-enzymatic chewable dentifrice which contains, for example, glucose and glucose oxidase for producing hydrogen peroxide upon chewing the dentifrice and further contains a thiocyanate salt and lactoperoxidase for interacting with hydrogen peroxide to produce a hypothiocyanate (sic) bacterial inhibitor, with pre-application stability being maintained by limiting any unbound water in the chewable dentifrice to an amount not more than about 1.0 wt. % and limiting the total water, bound and unbound, to not more than about 10 wt. %.

U.S. Pat. No. 4,578,365 (Pellico et al., 1986) discloses a di-enzymatic dentifrice which contains, for example, glucose and glucose oxidase for producing hydrogen peroxide upon oral application of the dentifrice and further contains a thiocyanate salt and lactoperoxidase for interacting with hydrogen peroxide to produce a hypothiocyanate (sic) with pre-application stability being maintained by limiting any water in the dentifrice to not more than about 10 wt. % based on the weight of the dentifrice.

U.S. Pat. No. 4,617,190 (Montgomery, 1986) discloses enzymatic powder milk which contains, for example, glucose, glucose oxidase, a peroxidase and potassium iodide for producing hypoiodite, an anionic bacterial inhibitor in the reconstituted milk.

U.S. Pat. No. 5,336,494 (Pellico, 1994) discloses an orally chewable, enzymatically coated pet product which contains, for example, Beta-D-glucose and glucose oxidase for producing hydrogen peroxide upon oral chewing of the product and may further contain a peroxidase and an alkali metal salt of an oxygen accepting anion such as potassium iodide for interacting with hydrogen peroxide to produce hypoiodite, an anionic bacterial inhibitor.

U.S. Pat. No. 5,453,284 (Pellico, 1995) discloses an aqueous enzymatic dentifrice having a water content in excess of 10 Wt. % and which contains, for example, Beta-D-glucose and glucose oxidase for producing hydrogen peroxide upon oral application of the dentifrice and may further contain a peroxidase and an oxidizable alkali metal salt such as the thiocyanate, chloride or iodide salt of sodium or potassium for interacting with hydrogen peroxide to produce an anionic bacterial inhibitor, with pre-application stability being maintained by the addition of a water soluble thickener in an amount to provide the dentifrice with a viscosity from about 800 to about 75,000 centipoises.

Each of the foregoing patent references is incorporated herein by reference thereto.

It would be very advantageous to provide a method for treatment of otitis externa with an enzymatic biocidal composition which is particularly adapted for use in the environment of the outer ear.

SUMMARY OF THE INVENTION

In accordance with this invention, there is provided a method for treating outer ear infection in dogs and cats, otitis externa, which comprises:

administering to an infected outer ear a dosage effective amount of a substantially non-aqueous di-enzymatic therapeutic composition in a liquid or gel fluid carrier; said therapeutic composition comprising, per gram of composition, from about 0.015 to about 0.6 millimole of oxidizable substrate and from about 0.5 to about 500 International Units of an oxidoreductase enzyme specific to such substrate for producing hydrogen peroxide upon administration to the outer ear and further containing from about 0.0001 to about 0.01 millimole of an iodide salt and from about 0.05 to about 20 International Units of peroxidatic peroxidase selected from the group consisting of lactoperoxidase, horse radish peroxidase, iodide peroxidase, myeloperoxidase and mixtures thereof for interacting with hydrogen peroxide to produce a hypoiodite pathogenic inhibitor; and limiting any unbound water present to an amount not more than about 1.0 wt. % based on the weight of the therapeutic composition to stabilize the composition against the production of hydrogen peroxide prior to aural application of the same and to enhance efficacy at the infectious site.

DETAILED DESCRIPTION

The invention described herein for the treatment of otitis externa is directed to the use of a substantially anhydrous liquid or gel carrier containing a hydro-activated and/or oxygen activated di-enzymatic system for producing potassium iodite, a biocidal agent, upon application to the outer ear. While the enzyme system in the liquid or gel therapeutic composition is dependent upon moisture and/or oxygen in the outer ear for activation, it is essential that the fluidic carrier be substantially anhydrous so as to maintain preapplication stability and, most importantly, the fluid carrier should not add any significant quantity of water to the ear which can promote the growth of microorganisms.

The enzymatic component of the therapeutic composition comprises a first enzyme system containing an oxidizable substrate and an oxidoreductase enzyme specific to such substrate for producing hydrogen peroxide upon application to the outer ear, with the chemical environment of the outer ear providing the source of additional reactant (oxygen) or reactants (oxygen, water) to effect the enzymatic reaction. Illustrative examples of oxidoreductase enzymes and their corresponding oxidizable substrates are set forth in the following table:

TABLE A

| OXIDOREDUCTASE ENZYME | OXIDIZABLE SUBSTRATE |
| --- | --- |
| Glucose oxidase | B-D-glucose |
| Hexose Oxidase | Hexose |
| Galactose Oxidase | D-galactose |
| Pyranose Oxidase | Pyranose |
| Pyruvate Oxidase | Pyruvate |
| Oxalate Oxidase | Oxalate |
| DL-Aminoacid Oxidase | DL-Aminoacid |

In an illustrative reaction, glucose oxidase catalyzes the interaction of Beta-D-glucose, water and oxygen during application to the outer ear to produce hydrogen peroxide and gluconic acid.

Glucose oxidase is characterized in the literature as a glycoprotein containing two molecules of flavine-adenine dinucleotide which has a molecular weight of approximately 150,000, an isoelectric point at pH 4.2 and an optimum pH at 5.5 with a broad pH range from 4 through 7.

The oxidizable substrate is generally present in the therapeutic composition in an amount from about 0.015 to about 0.6 millimole per gram of therapeutic composition and, preferably, in an amount from about 0.025 to about 0.1 millimole per gram of therapeutic composition while the oxidoreductase enzyme specific to the substrate is generally present in the composition in an amount from about 0.5 to about 500 International Units (herein sometimes abbreviated IU) per gram of composition, and, preferably, in an amount from about 10 to about 40 IU per gram of composition. The term millimole identifies that quantity in grams corresponding to the molecular weight of the composition divided by one thousand. The term International Unit(s) identifies that amount of enzyme that will effect catalysis of 1.0 micromole of substrate per unit at pH 7.0 and 25 C. Oxidoreductase enzymes are supplied in dry or liquid form with the label specifying the concentration in International Units on a per gram or per milliliter, as appropriate.

In addition to the first enzyme system comprising oxidizable substrate and oxidoreductase enzyme specific to such substrate for producing hydrogen peroxide, the enzymatic therapeutic composition of this invention is provided with a second enzyme system containing a peroxidatic peroxidase and an alkali metal salt of an oxygen accepting anion for interacting with hydrogen peroxide to produce an oxidized anionic biocidal agent.

Peroxidases which can be used in the practice of this invention include lactoperoxidase, horseradish peroxidase, iodide peroxidase, and myeloperoxidase. Oxidizable salts which are particularly useful in this invention include the iodide salt of potassium, sodium or ammonium or mixtures thereof. In the presence of hydrogen peroxide, the oxygen accepting anion of the aforesaid salts, namely, iodide, is oxidized to hypoiodite, a biocidal agent.

Lactoperoxidase is a glycoprotein which, in one commercial embodiment, is a lyophilized powder derived from milk. This commercial peroxidase has an activity of 80 IU/mg and a projected molecular weight of 93,000 for L-Tyrosine Iodination. The physical-chemical properties reported for lactoperoxidase include: molecular weight 78,000; partial specific volume 0.74; and heme/mole 1.0.

The peroxidase is generally present in the therapeutic composition in an amount from about 0.05 to about 20 International Units per gram of composition and, preferably, in an amount from about 0.1 to about 1.0 International Units per gram of composition while the oxidizable salt is generally present in the composition in an amount from about 0.0001 to about 0.01 millimole per gram of composition and, preferably, in an amount from about 0.001 to about 0.006 millimole per gram of composition.

The operable integrity of the enzymatic system can be affected by catalase which is present in commercial glucose oxidase as well as mucous membrane tissue. Catalase, which is extraneous to the enzymatic system of this invention, competes with peroxidatic peroxidase for hydrogen peroxide. In order to reduce loss of hydrogen peroxide through the presence of catalase, an effective amount of enzymatic inhibitor specific to catalase can be advantageously incorporated into the enzymatic composition. An ascorbic salt such as sodium ascorbate, potassium ascorbate, ascorbyl palmitate, or mixtures thereof can be used as an enzymatic inhibitor which is specific to catalase. An effective amount of ascorbate salt for catalase inhibition is from about 0.000001 to about 0.0001 millimole per gram of therapeutic composition. Iron salts such as ferrous sulfate can be incorporated the enzymatic composition as a potentiator for ascorbate salt in its role as catalase inhibitor.

The enzymatic therapeutic compositions of this invention may advantageously be formulated with an aminohexose as, for example, an aminoglucose such as glucosamine, N-actyl glucosamine or mixtures thereof in order to increase the yield or accumulation of oxidized anionic biocidal agent. The aminoglucose is generally present in the enzymatic composition in an amount from about 0.001 to about 0.002 millimole per gram of composition and, preferably, in amount from about 0.003 to about 0.001 millimole per gram of composition.

Since water promotes the oxidation/reduction reactions of this invention and is also a reactant in certain reactions, the use of water in formulating the di-enzymatic therapeutic compositions should be at a relatively low concentration level in order to stabilize the composition against the production of hydrogen peroxide prior to aural application of the same and to enhance efficacy at the infectious site. For this purpose, it has been found to be essential to limit any unbound water present in the composition to an amount not more than about 1.0 wt. % and, preferably, to an amount not more than about 0.5 wt. % and, optimally, to an amount not more than about 0.25 wt. %; and, further, to limit the total water, bound and unbound, to not more than about 10 wt. %.

The fluid carriers which can be used in the practice of this invention advantageously include glycerol, propylene glycol, mixtures thereof and equivalents thereto. The fluid carrier is generally present in the composition in an amount from about 80 to about 96 wt. % and, preferably, in an amount from about 90 to about 96 wt. %. The fluid carrier and concentration thereof are so selected as to provide the composition with appropriate pressure responsive application characteristics.

Where the products of the activated enzyme system include a weak organic acid, it is advantageous to formulate the composition with a buffering agent to neutralize the organic acid. A suitable buffering agent is sodium stearate which can be present in the composition in an amount up to about 6.0 wt. % as, for example, in an amount from about 2 to about 6 wt. %.

Adjunct therapeutic agents such as the enzyme lysozyme and the protein lactoferrin as well as hydrocortisone and benzyl alcohol can be added to the enzymatic formulations of this invention.

Klucel, the trademark for hydroxypropyl methylcellulose stabilizer and thickener, (Merck Index, 12th ed., Monograph No. 4889), can be added to the enzymatic compositions for beneficial flow and application characteristics.

The di-enzymatic therapeutic composition in the form of a flowable liquid can be prepared in any suitable manner as, for example, by blending the dry ingredients into the liquid ingredients, with agitation, until a uniform mixture is obtained, with the proviso that sheer sensitive ingredients, which include the enzymes, are added last to minimize shear impact on such ingredients. Following formulation of the composition, the flowable liquid can be loaded into a suitable dispenser for application to the outer ear of dogs and cats for treatment of otitis externa.

EXAMPLES

The following examples, enzymatic liquids, further illustrate the Invention. The enzymes specified in the di-enzymatic systems in the examples, namely, glucose oxidase, D-amino acid oxidase, D-glutamate oxidase and lactoperoxidase had an activity of 100,000 International Units per gram.

Example 1

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Potassium iodide | 0.045 |
| Beta-D-glucose | 0.301 |
| D.I. Water | 0.150 |
| Glucose oxidase | 0.001 |
| Lactoferrin | 0.008 |
| Lysozyme | 0.008 |
| Lactoperoxidase | 0.008 |
| | 100.00 |

Example 2

| Composition | Weight, grams |
|---|---|
| Glycerol USP | 35.410 |
| Propylene glycol | 58.623 |
| Klucel MFF | 1.440 |
| Benzyl alcohol NF | 3.006 |
| Hydrocortisone | 1.000 |
| Potassium iodide | 0.045 |
| Beta-D-glucose | 0.301 |
| D.I. Water | 0.150 |
| Glucose oxidase | 0.001 |
| Lactoferrin | 0.008 |
| Lysozyme | 0.008 |
| Lactoperoxidase | 0.008 |
| | 100.00 |

Example 3

| Composition | Weight, grams |
|---|---|
| Glycerol USP | 15.410 |
| Propylene glycol | 79.623 |
| Benzyl alcohol NF | 3.006 |
| Hydrocortisone | 1.000 |
| Potassium iodide | 0.045 |
| Beta-D-glucose | 0.301 |
| D.I. Water | 0.150 |
| Glucose oxidase | 0.001 |
| Lactoferrin | 0.008 |
| Lysozyme | 0.008 |
| Lactoperoxidase | 0.008 |
| | 99.56 |

Example 4

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |

-continued

| Composition | Weight, grams |
|---|---|
| Potassium iodide | 0.045 |
| Beta-D-glucose | 0.301 |
| D.I. Water | 0.150 |
| Glucose oxidase | 0.001 |
| Lactoferrin | 0.008 |
| Lysozyme | 0.008 |
| Lactoperoxidase | 0.008 |
| | 100.00 |

Example 5

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Potassium iodide | 0.045 |
| D-Alamine | 0.500 |
| D.I. Water | 0.150 |
| D-Amino acid oxidase | 0.100 |
| Lactoferrin | 0.008 |
| Lysozyme | 0.008 |
| Lactoperoxidase | 0.008 |
| | 100.703 |

Example 6

| Composition | Weight, grams |
|---|---|
| Glycerol USP | 15.410 |
| Propylene glycol | 79.623 |
| Klucel MFF | 1.440 |
| Benzyl alcohol NF | 3.006 |
| Hydrocortisone | 1.000 |
| Potassium iodide | 0.010 |
| Beta-D-glucose | 0.500 |
| D.I. Water | 0.150 |
| Glucose oxidase | 0.070 |
| Lactoferrin | 0.008 |
| Lysozyme | 0.008 |
| Lactoperoxidase | 0.002 |
| | 100.227 |

Example 7

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Potassium iodide | 0.010 |
| Dextrose | 0.301 |

-continued

| Composition | Weight, grams |
|---|---|
| D.I. Water | 0.150 |
| Glucose oxidase | 0.001 |
| Lactoferrin | 0.008 |
| Lysozyme | 0.008 |
| Lactoperoxidase | 0.010 |
| | 99.967 |

Example 8

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Potassium iodide | 0.045 |
| D-glutamate | 0.301 |
| D.I. Water | 0.150 |
| D-Glutamate oxidase | 0.010 |
| Lactoferrin | 0.008 |
| Lysozyme | 0.008 |
| Lactoperoxidase | 0.008 |
| | 100.009 |

Example 9

| Composition | Weight, grams |
|---|---|
| Glycerol USP | 15.4100 |
| Propylene glycol | 79.6230 |
| Klucel MFF | 0.4400 |
| Benzyl alcohol NF | 3.0060 |
| Hydrocortisone | 1.0000 |
| Potassium iodide | 0.0450 |
| Beta-D-Glucose | 0.5000 |
| D.I. Water | 0.1500 |
| Glucose oxidase | 0.0008 |
| Lactoferrin | 0.0080 |
| Lysozyme | 0.0080 |
| Lactoperoxidase | 0.0080 |
| | 100.1988 |

Example 10

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Ammonium iodide | 0.045 |
| Dextrose | 0.301 |
| D.I. Water | 0.150 |
| Glucose oxidase | 0.001 |

-continued

| Composition | Weight, grams |
|---|---|
| Lactoferrin | 0.008 |
| Lysozyme | 0.008 |
| Lactoperoxidase | 0.008 |
| | 100.000 |

Example 11

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Sodium iodide | 0.010 |
| Beta-D-Glucose | 6.000 |
| D.I. Water | 0.150 |
| Glucose oxidase | 0.400 |
| Lactoferrin | 0.008 |
| Lysozyme | 0.008 |
| Lactoperoxidase | 0.001 |
| | 106.056 |

Example 12

| Composition | Weight, grams |
|---|---|
| Glycerol USP | 15.4100 |
| Propylene glycol | 79.6230 |
| Klucel MFF | 0.4400 |
| Benzyl alcohol NF | 3.0060 |
| Hydrocortisone | 1.0000 |
| Potassium iodide | 0.0450 |
| Beta-D-Glucose | 1.5000 |
| D.I. Water | 0.1500 |
| Glucose oxidase | 0.0250 |
| Lactoferrin | 0.0080 |
| Lysozyme | 0.0080 |
| Lactoperoxidase | 0.0005 |
| | 101.4405 |

Example 13

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Potassium iodide | 0.045 |
| Beta-D-Glucose | 2.000 |
| D.I. Water | 0.150 |
| Glucose oxidase | 0.020 |
| Lactoferrin | 0.008 |
| Lysozyme | 0.008 |
| Lactoperoxidase | 0.010 |
| | 101.720 |

Example 14

| Composition | Weight, grams |
|---|---|
| Glycerol USP | 15.410 |
| Propylene glycol | 79.623 |
| Klucel MFF | 0.440 |
| Benzyl alcohol NF | 3.006 |
| Hydrocortisone | 1.000 |
| Potassium iodide | 0.045 |
| Beta-D-Glucose | 1.500 |
| D.I. Water | 0.150 |
| Glucose oxidase | 0.040 |
| Lactoferrin | 0.008 |
| Lysozyme | 0.008 |
| Lactoperoxidase | 0.012 |
| Glucosamine | 0.012 |
| N-Acetylglucosamine | 0.010 |
| | 101.264 |

In view of the foregoing description and examples, it will become apparent to those of ordinary skill in the art that equivalent modifications thereof may be made without departing from the spirit and scope of this invention.

That which is claimed is:

1. A method for treating otitis externa outer ear infection in dogs and cats, which comprises:
    administering to an infected outer ear a dosage effective amount of a substantially non-aqueous therapeutic composition in a fluid carrier,
    said fluid carrier being a member selected from the group consisting of glycerol, propylene glycol, and mixtures thereof, wherein the concentration of the fluid carrier in the therapeutic composition is from about 80 to about 96 wt. % based on the weight of the therapeutic composition,
    said therapeutic composition comprising, per gram, from about 0.015 to about 0.6 millimole of oxidizable substrate and from about 0.5 to about 500 International Units of an oxidoreductase enzyme specific to said substrate for producing hydrogen peroxide upon administration to the outer ear and further containing from about 0.0001 to about 0.01 millimole of an iodide salt and from about 0.05 to about 20 International Units of peroxidatic peroxidase selected from the group consisting of lactoperoxidase, horse radish peroxidase, iodide peroxidase, myeloperoxidase and mixtures thereof for interacting with hydrogen peroxide to produce a hypoiodite biocidal agent; and
    limiting any unbound water present to an amount not more than about 1.0 wt. % based on the weight of the therapeutic composition to stabilize the composition against the production of hydrogen peroxide prior to administering said cccomposition to said outer ear.

2. The method of claim 1 wherein any unbound water present in the therapeutic composition is limited to an amount not more than about 0.5 wt. % based on the weight of the composition.

3. The method of claim 1 wherein any unbound water present in the therapeutic composition is limited to an amount not more than about 0.25 wt. % based on the weight of the composition.

4. The method of claim 1 wherein the concentration of the fluid carrier in the therapeutic composition is from about 90 to about 96 wt. % based on the weight of the composition.

5. The method of claim 1 wherein the iodide salt is selected from the group consisting of potassium iodide, sodium iodide, ammonium iodide and mixtures thereof.

6. The method of claim 5 wherein the iodide salt is potassium iodide.

7. The method of claim 5 wherein the iodide salt is sodium iodide.

8. The method of claim 1 wherein the oxidizable substrate is B-D-glucose and the oxidoreductase enzyme is glucose oxidase.

9. The method of claim 1 wherein the oxidizable substrate is D-alanine and the oxidoreductase enzyme is D-amino acid oxidase.

10. The method of claim 1 wherein the oxidizable substrate is dextrose and the oxidoreductase enzyme is glucose oxidase.

11. The method of claim 1 wherein the oxidizable substrate is D-glumate and the oxidoreductase enzyme is D-glumate oxidase.

12. The method of claim 1 wherein the oxidizable substrate is present in an amount from about 0.025 to about 0.1 millimole, the oxidoreductase enzyme specific to the substrate is present in an amount from about 10 to about 40 International Units, the peroxidase is present in an amount from about 0.1 to about 1.0 International Units, and the iodide salt is present in an amount from about 0.001 to about 0.006 millimole, wherein each amount is per gram of the therapeutic composition.

13. The method of claim 12 which further contains an effective amount of an augmenting anti-bacterial agent selected from the group consisting of lysozyme, lactoferrin, and mixtures thereof.

14. The method of claim 12 which further includes a compatible thickener for imparting a suitable viscosity to the therapeutic composition for administering to said outer ear.

15. The method of claim 12 further which includes an aminoglucose selected from the group consisting of glucosamine, N-acetyl glucosamine and mixtures thereof in an amount from about 0.0003 to about 0.001 millimole per gram of therapeutic composition.

* * * * *